United States Patent
Hashimoto et al.

(10) Patent No.: US 10,016,317 B2
(45) Date of Patent: Jul. 10, 2018

(54) PULL-ON DISPOSABLE WEARING ARTICLE

(71) Applicant: UNICHARM CORPORATION, Shikokuchuo-shi, Ehime (JP)

(72) Inventors: Tatsuya Hashimoto, Kanonji (JP); Tetsuo Okubo, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 278 days.

(21) Appl. No.: 14/773,381

(22) PCT Filed: Feb. 19, 2014

(86) PCT No.: PCT/JP2014/053878
§ 371 (c)(1),
(2) Date: Sep. 7, 2015

(87) PCT Pub. No.: WO2014/136577
PCT Pub. Date: Sep. 12, 2014

(65) Prior Publication Data
US 2016/0022510 A1    Jan. 28, 2016

(30) Foreign Application Priority Data
Mar. 8, 2013 (JP) .................. 2013-047405

(51) Int. Cl.
*A61F 13/49* (2006.01)
*A61F 13/493* (2006.01)
(Continued)

(52) U.S. Cl.
CPC ...... *A61F 13/496* (2013.01); *A61F 13/15804* (2013.01); *A61F 13/49406* (2013.01)

(58) Field of Classification Search
CPC .............. A61F 13/15804; A61F 13/496; A61F 13/49406
See application file for complete search history.

(56) References Cited

U.S. PATENT DOCUMENTS 5,911,713 A    6/1999   Yamada et al.
6,248,097 B1   6/2001   Beitz et al.
(Continued)

FOREIGN PATENT DOCUMENTS

EP    0648482 A2    4/1995
EP    0648482 A3    10/1996
(Continued)

OTHER PUBLICATIONS

International Search Report dated May 20, 2014, in International Application No. PCT/JP2014/053878.
(Continued)

*Primary Examiner* — Leslie Deak
*Assistant Examiner* — Gabriella Burnette
(74) *Attorney, Agent, or Firm* — Hauptman Ham, LLP

(57) ABSTRACT

A pull-on disposable wearing article having leg-openings of sufficient size to assure that respective peripheries of the leg-openings to reliably cover the wearer's buttocks without apprehension that the peripheries of the leg-openings might collapse inward. A crotch panel at least includes an absorbent structure located on a skin-facing surface of a crotch region and a pair of elastic side flaps extending outward in a transverse direction from both side edges of the absorbent structure. The elastic side flaps have inelastic regions defined on the outer sides in the transverse direction of both side edges of the absorbent structure and elastic regions defined on the outer sides in the transverse direction of the respective inelastic regions. The crotch panel has a dimension in the transverse direction corresponding to about 55 to about 70% of a dimension in the transverse direction of the front and rear waist regions.

6 Claims, 10 Drawing Sheets

(51) Int. Cl.
  *A61F 13/494* (2006.01)
  *A61F 13/496* (2006.01)
  *A61F 13/15* (2006.01)

(56) References Cited

U.S. PATENT DOCUMENTS

| | | |
|---|---|---|
| 7,972,316 B2 | 7/2011 | Toyoshima et al. |
| 8,518,008 B2 | 8/2013 | Yoshioka et al. |
| 2007/0287975 A1 | 12/2007 | Fujimoto et al. |
| 2009/0088718 A1 | 4/2009 | Toyoshima et al. |
| 2010/0324519 A1* | 12/2010 | Shimada ............ A61F 13/49011 604/385.3 |
| 2012/0116343 A1 | 5/2012 | Yoshioka et al. |

FOREIGN PATENT DOCUMENTS

| | | |
|---|---|---|
| FR | 2816204 A1 | 5/2002 |
| JP | 8-66424 A | 3/1996 |
| JP | 2002-522117 A | 7/2002 |
| JP | 3830545 B2 | 10/2006 |
| JP | 2006-341061 A | 12/2006 |
| JP | 3857292 B1 | 12/2006 |
| JP | 2007-29482 A | 2/2007 |
| JP | 2008-508082 A | 3/2008 |
| JP | 2009-539467 A | 11/2009 |
| JP | 4521118 B2 | 8/2010 |
| JP | 4662463 B2 | 3/2011 |
| JP | 2011-110317 A | 6/2011 |
| JP | 2011110317 A * | 6/2011 |
| JP | 2012-101063 A | 5/2012 |
| JP | 4948673 B2 | 6/2012 |
| JP | 4980420 B2 | 7/2012 |
| JP | 2012-228423 A | 11/2012 |
| JP | 5303689 B1 | 10/2013 |
| JP | 2013-226392 A | 11/2013 |
| WO | 2006/120847 A1 | 11/2006 |

OTHER PUBLICATIONS

Extended European Search Report in EP Application No. 14760643.8, dated Feb. 22, 2016.

Office Action in JP Application No. 2013-047405, dated Aug. 9, 2016.

Decision to Grant a Patent in JP Application No. 2013-047405, dated Mar. 7, 2017.

* cited by examiner

PULL-ON DISPOSABLE WEARING ARTICLE

RELATED APPLICATIONS

The present application is a National Phase of International Application Number PCT/JP2014/053878, filed Feb. 19, 2014, which claims priority to Japanese Application Number 2013-047405, filed Mar. 8, 2013.

TECHNICAL FIELD

The present invention relates to pull-on disposable wearing articles and, in more detail, to pull-on disposable wearing articles such as pull-on disposable diaper, disposable toilet-training pants and disposable incontinence disposable pants each having elastic leg-openings.

BACKGROUND

Conventionally, the pull-on disposable wearing articles are known having the elastic leg-openings. For example, Patent Literature 1 discloses a pull-on disposable wearing article having an elastic waist panel, a crotch panel joined to a skin-facing surface of the elastic waist panel, a liquid-absorbent structure extending across a crotch region into front and rear waist regions and, in the rear waist region, buttocks-covering regions extending from seams toward the crotch region along which respective both side edges of the front and rear waist regions are joined to each other. A pair of elastic cuffs respectively elasticized by a plurality of elastic elements are arranged along the both side edge portions of the crotch region.

CITATION LIST

Patent Literature

{PTL 1}: JP 2008-508082 A

SUMMARY

Technical Problem

According to the disclosure of the Patent Literature 1, with the pull-on disposable wearing article put on the wearer's body, the buttocks-covering regions extending downward from the seams toward the crotch region in the rear waist region cover the wearer's buttocks and the elastic cuffs rise so as to be put in close contact with the wearer's thighs at a desired degree of fit to prevent body exudates from leaking sideways.

However, the elastic cuffs may be kept in close contact with the wearer's thighs at the desired degree of fit only in regions of the respective elastic cuffs in which elastic elements are present and the remaining regions may collapse inward and be tucked between the thighs and/or in cleavage of the buttocks until the buttocks may be partially exposed to the outside. To avoid such undesirable situation, it will be possible to broaden the width dimension of the crotch panel, thereby ensuring that the elastic cuffs will not be tucked between the thighs even if the elastic cuffs collapse inward. In this situation, however, sizes of the respective leg-openings will be correspondingly constrained and the wearer's toes may be caught by part of the crotch panel when a wearer or a care person inserts the wearer's legs into the leg-openings to put the diaper on the wearer's body.

In particular, in the pull-on disposable wearing article of three connecting piece structure composed of the front waist panel defining the front waist region, the rear waist panel defining the rear waist region and the liquid-absorbent structure of which the front and rear end portions are fixed to the front and rear waist panels, respectively, the leg-openings are apt to be tucked in the buttock-cleavage of the wearer and the problems mentioned above further stand out.

An object of the present invention is to improve the conventional disposable wearing articles, thereby providing a pull-on disposable wearing articles having leg-openings of sufficient size and assuring that respective leg-openings reliably cover the wearer's buttocks so that the peripheries of the leg-openings do not collapse inward.

Solution to Problem

The present invention to solve the problem set forth above is directed to a pull-on disposable wearing article having a longitudinal direction and a transverse direction and including skin-facing surface/non-skin-facing surfaces, a front waist region, a rear waist region, a crotch region extending between the front and rear waist regions, a front waist panel defining the front waist region, a rear waist panel defining the rear waist region, a crotch panel defining the crotch region and an absorbent structure attached to the skin-facing surface of the crotch panel and extending across the crotch region into the front and rear waist regions.

The present invention features the pull-on disposable wearing article, wherein the elastic front and rear waist panels respectively have elastic regions defined on the outer side in the transverse direction of front and rear end portions of the absorbent structure and inelastic regions defined in a region in which the absorbent structure is present; the crotch panel has a pair of elastic side flaps located outward of both side edges of the absorbent structure as viewed in the transverse direction and extending in the longitudinal direction; each of the elastic side flaps has front and rear end portions fixed to the front and rear waist regions so as to extend outward in the transverse direction, inelastic regions defined outward of each of both side edges of the absorbent structure as viewed in the transverse direction and an elastic region defined outward of the inelastic region as viewed in the transverse direction; and a dimensional ratio in the transverse direction of the crotch panel versus a dimension in the transverse direction of the front and rear waist regions is in a range of about 55 to about 70%.

Advantageous Effects of Invention

In the pull-on disposable wearing article according to the present invention, a ratio of the dimension in the transverse direction of the crotch panel versus the dimension in the transverse direction of the front and rear waist regions is in a range of about 55 to about 70% and such ratio is sufficient to cover the wearer's buttocks in the area of the crotch region adjacent to the rear waist region. Further, in the elastic side flaps, the inelastic regions rise toward the wearer's body to prevent leakage of body exudates and the elastic regions project outward in the transverse direction and are kept in contact in planar state with the thighs. In this manner, the elastic regions should not be tucked in the cleavage of the buttocks and/or the leg-openings should not be narrowed and the wearer's toe should not be caught by the leg-opening in the course of putting the article on the wearer's body.

BRIEF DESCRIPTION OF DRAWINGS

The drawings illustrate specific embodiments of the present invention, including optional and preferred embodiments as well as essential features of the invention.

DESCRIPTION OF EMBODIMENTS

The embodiments described below relate to a disposable diaper illustrated in FIGS. 1 through 10 as an example of the pull-on disposable wearing article according to the present invention, including both optional and preferred features as well as those features which are essential features of the present invention.

First Embodiment

Figure 1:
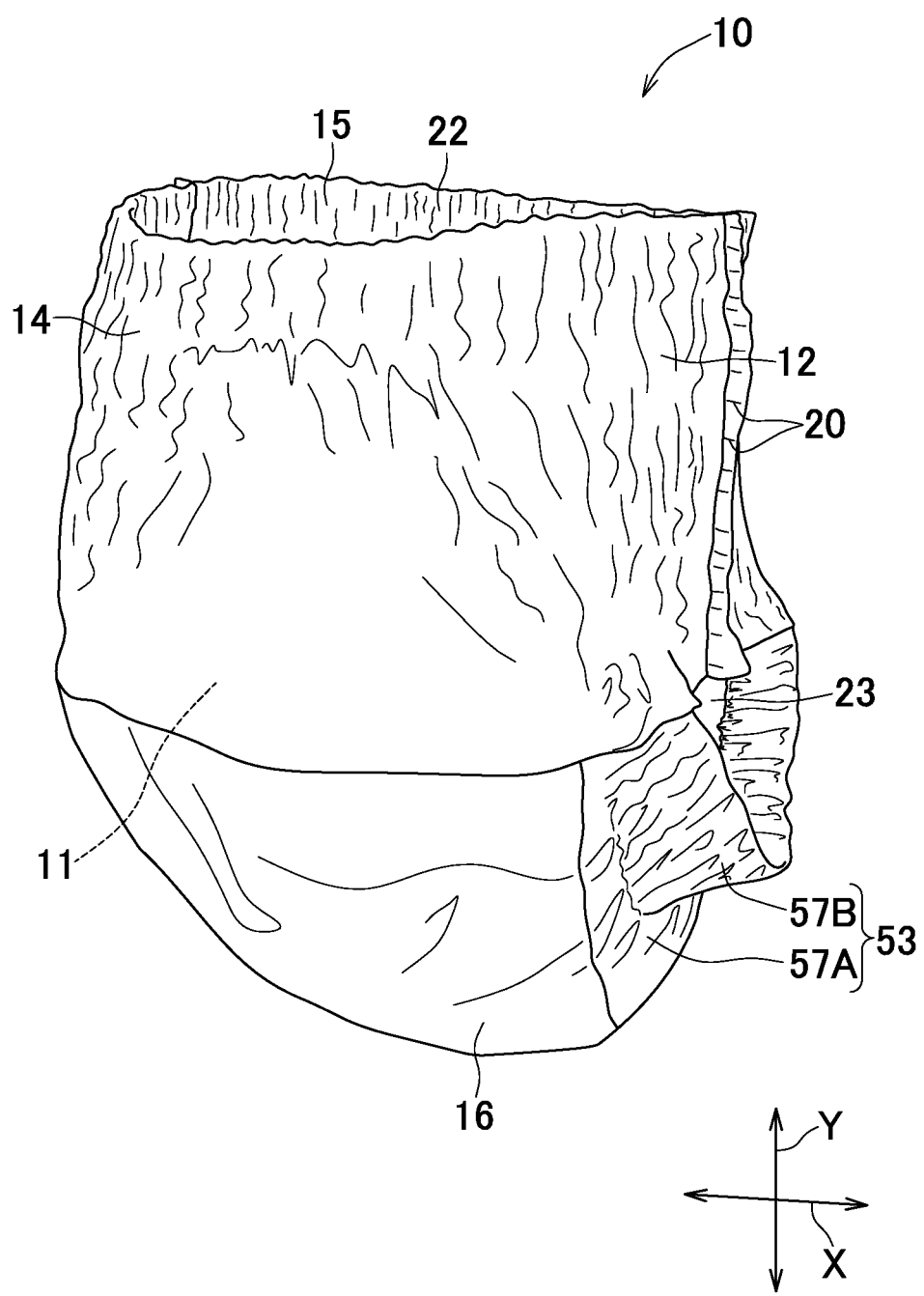
FIG. 1 is a perspective view illustrating a disposable diaper according to a first embodiment as an example of a pull-on disposable wearing article according to the present invention.
Figure 2:
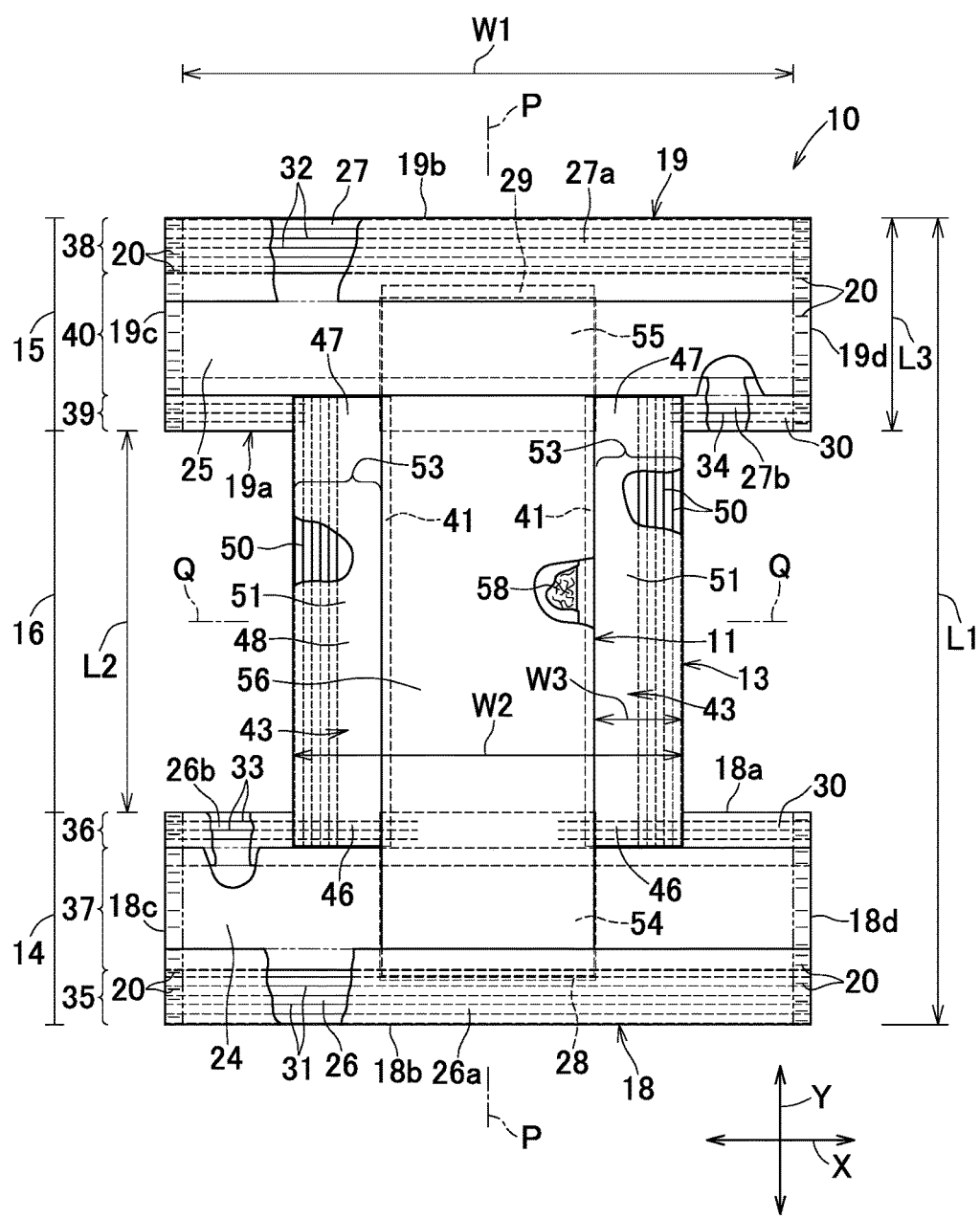
FIG. 2 is a partially cutaway plan view of the diaper developed in longitudinal and transverse directions to the maximum extensibility of respective elastic elements.
Figure 3:
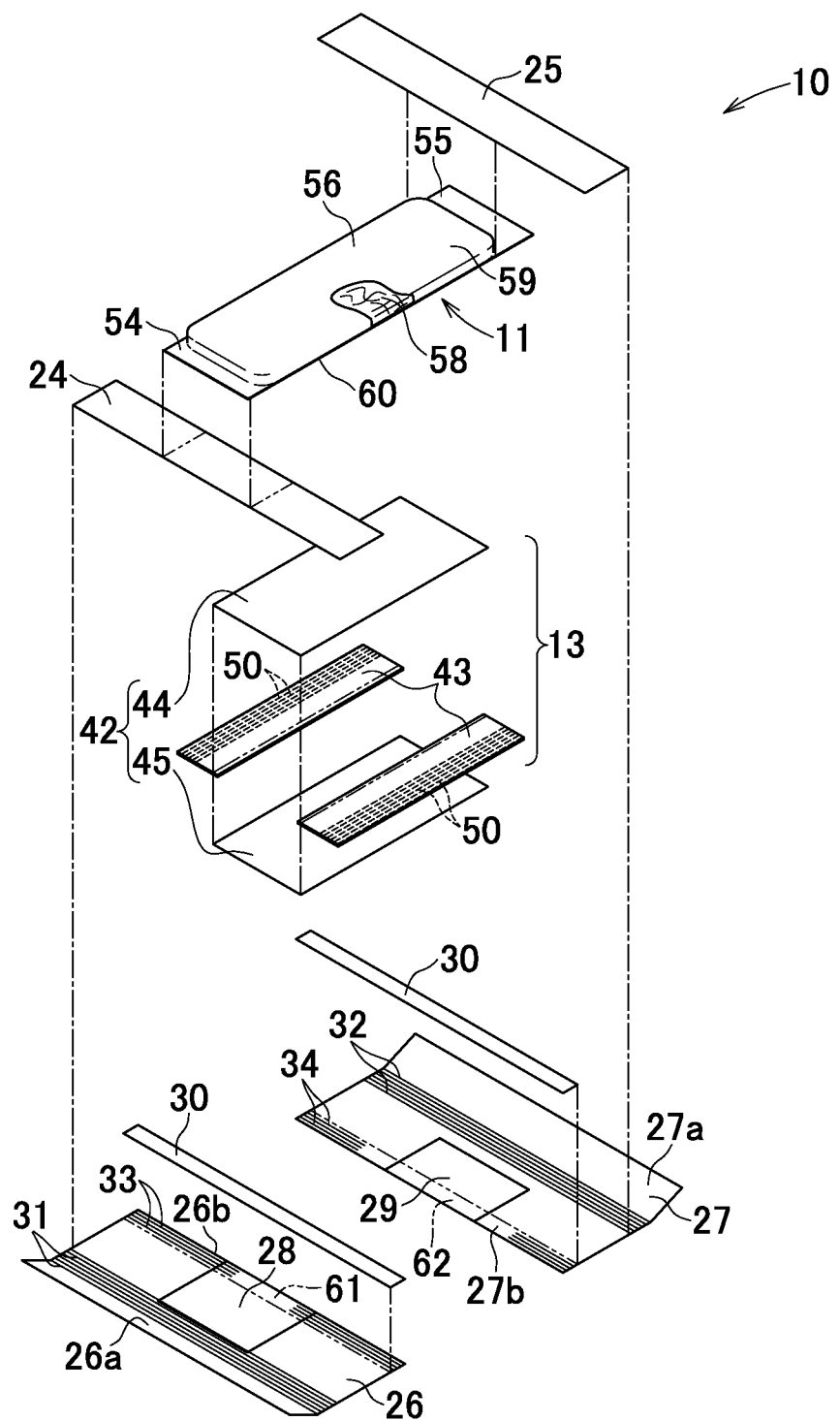
FIG. 3 is a partially cutaway exploded perspective view of the diaper.
Figure 4:
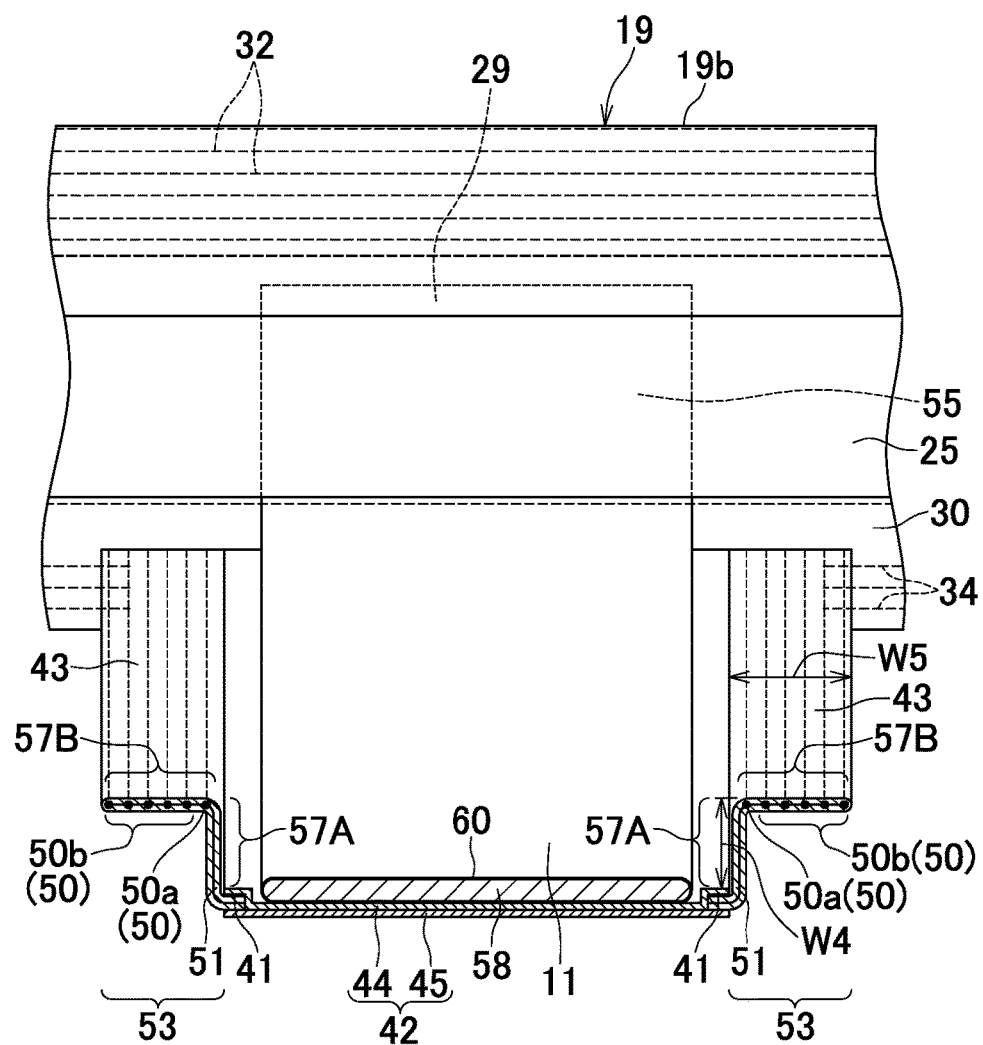
FIG. 4 is partial sectional view of a crotch region of the diaper put on the wearer's body.

Referring to FIGS. 1 through 3, a disposable diaper 10 as an example of a pull-on disposable wearing article according to the present invention has a longitudinal axis P, a transverse axis Q, a longitudinal direction Y and a transverse direction X, and includes a skin-facing surface, a non-skin-facing surface opposite to the skin-facing surface, an annular elastic waist panel 12 circumferentially extending around the wearer's waist, a liquid-absorbent structure 11 fixedly disposed on the respective skin-facing surfaces of the annular elastic waist panel 12 and an elastic crotch panel 13 attached to the skin-facing surface of the elastic waist panel 12. The diaper 10 has a front waist region 14, a rear waist region 15 and a crotch region 16 extending between the front and rear waist regions 14, 15, and is symmetric about the longitudinal axis P.

<Elastic Waist Panel>

The elastic waist panel 12 functions as an elastic belt to hold the liquid-absorbent structure 11 in a crotch region of the wearer and has a front waist panel 18 defining the front waist region 14 and a rear waist panel 19 defining the rear waist region 15. The front waist panel 18 has a laterally longer rectangular shape contoured by an inner end edge 18a, an outer end edge 18b, and both side edges 18c, 18d extending between the inner and outer end edges 18a and 18b. The rear waist panel 19 has a laterally longer rectangular shape contoured by an inner end edge 19a, an outer end edge 19b, and both side edges 19c, 19d extending between the inner and outer end edges 19a and 19b. The both side edges 18c, 18d of the front waist panel 18 are joined to the corresponding both side edges 19c, 19d of the rear waist panel 19 at seams 20 continually formed in the longitudinal direction Y with use of well known techniques, for example, thermal fusion bonding techniques such as hot embossing/debossing or ultrasonic processing so as to form a waist-opening 22 and a pair of leg-openings 23. As will be apparent from the arrangement described above, according to the present invention, the front and rear waist panels 18, 19 are joined to each other along the respective both side edge portions at the seams 20. The respective inner end edges 18a, 19a mean respective lower ends of junction lines defined by two row of the seams 20, instead of the positions closer to the crotch region 16 beyond these lower ends.

The front and rear waist panels 18, 19 respectively include waist interior layers 24, 25 lying on the side of the skin-facing surface and waist exterior layers 26, 27 lying on the side of the non-skin-facing surface. The waist exterior layers 26, 27 are larger than the waist interior layers 24, 25 in a width dimension in the longitudinal direction Y and extend outward in the longitudinal direction Y beyond the interior and exterior end edges of the waist interior layers 24, 25.

<Waist Exterior Layer>

As material for the waist exterior layers 26, 27, SMS (spunbonded/meltblown/spunbonded) fibrous nonwoven fabrics, spunbonded nonwoven fabrics, air-through nonwoven fabrics, plastic films or laminate sheets formed of any one of various types of fibrous nonwoven fabrics described above and plastic sheets, each having a mass per unit area in a range of about 15 to about 30 g/m2 may be used. The waist interior layers 24, 25 are respectively joined to the waist exterior layers 26, 27, with hot melt adhesive distributed to the interior surface of at least one of the respective interior and exterior layers facing each other or with use of well known thermal fusion bonding techniques.

<Waist Interior Layer>

As material for the waist interior layers 24, 25, various types of well known elastic fibrous nonwoven fabrics such as spunbonded fibrous nonwoven fabrics, meltblown fibrous nonwoven fabrics, heat-roll fibrous nonwoven fabrics, SMS fibrous nonwoven fabrics, air-laid fibrous nonwoven fabrics or air-through fibrous nonwoven fabrics may be used independently or in combination. The elastic nonwoven fabrics may be formed from, for example, polyethylene-based or polyurethane-based elastomer resin or polyethylene-, polyester-based or acrylic thermoplastic resins. While it is possible to use inelastic fibrous nonwoven fabrics as material for the waist interior layers 24, 25, at least the waist interior layers 24, 25 are preferably formed of elastic fibrous nonwoven fabrics to improve flexibility and texture for the reason that, as will be described later in more detail, the waist interior layers 24, 25 are the layers put in directly contact with the wearer's skin.

<Graphic Patch>

Referring to FIGS. 2 and 3, graphic patches 28, 29 formed from plastic materials and having graphics (not shown) or the like displayed thereon so as to be visually recognizable through the non-skin-facing surface from the outside are interposed between the waist interior layers 24, 25 and the waist exterior layers 26, 27 in central regions of the front and rear waist regions 14, 15, respectively, as viewed in the transverse direction X.

\<Respective Waist Elastic Element\>

In the front and rear waist panels 18, 19, portions of the waist exterior layers 26, 27 extending outward in the longitudinal direction Y beyond the respective outer end edges of the waist interior layers 24, 25 are folded back inward and, within respective folded-back portions 26a, 27a, a plurality of strand- or string-like first and second waist-elastic elements 31, 32 are contractibly secured under tension and in contractible manner, for example, with hot melt adhesive. Meanwhile, fixing sheet strips 30 formed of fibrous nonwoven fabrics are arranged on respective prolongations 26b, 27b of the waist exterior layers 26, 27 further extending inward in the longitudinal direction Y from the respective inner end edges of the waist interior layers 24, 25 and strand- or string-like first and second waist inner end elastic elements 33, 34 are contractibly secured under tension, for example, with hot melt adhesive between the fixing sheet strips 30 and the prolongations 26b, 27b, respectively. As material for the first and second waist elastic elements 31, 32, and first and second waist inner end elastic elements 33, 34, it is possible to use, for example, string- or strand-like elastic material having fineness in a range of 310 to 780 dtex and a stretch ratio in a range of 2.0 to 3.5 times.

\<Front and Rear Waist Region\>

The front waist region 14 has an outer end portion 35 in which the first waist elastic elements 31 are arranged, an inner end portion 36 in which the first waist inner end elastic elements 33 are arranged and an intermediate portion 37 defined between the outer and inner end portions 35, 36. The rear waist region 15 has an outer end portion 38 in which the second waist elastic elements 32 are arranged, an inner end portion 39 in which the second waist inner end elastic elements 34 are arranged and an intermediate portion 40 defined between the outer and inner end portions 38, 39. In the respective intermediate portions 37, 40 including none of the elastic elements, the waist interior layers 24, 25 are respectively arranged. Such arrangement in the diaper put on the wearer's body ensures that the respective outer end portions 35, 38 and the respective inner end portions 36, 39 of the front and rear waist regions 14, 15 are stably kept in close contact with the wearer's body at desirable degrees of fit under contractile forces of the respective elastic elements and, the respective intermediate portions 37, 40 also are kept in close contact with the wearer's body at desirable degrees of fit under contractile force of the waist interior layers 24, 25. In consequence, the diaper 10 put on the wearer's body should not be displaced to an extent causing leakage of body exudates.

The first and second waist inner end elastic elements 33, 34 in the respective inner end portions 36, 39 of the front and rear waist regions 14, 15 are arranged so as to be distanced from each other in the transverse direction X and, between a pair of elastic regions in which these inner end elastic elements are arranged, inelastic regions 61, 62 in which none of the first and second waist inner end elastic elements 33, 34 is arranged are defined. The inelastic region 61 may be formed, for example, by arranging the first waist inner end elastic elements 33 in the inner end portion 36 so as to extend in the transverse direction X in their stretched states, then securing the first waist inner end elastic elements 33 to the inner end portion 36 with hot melt adhesive distributed to the inner end portion 36 except a central portion thereof and cutting the first waist inner end elastic elements 33 in this central portion whereupon the first waist inner end elastic elements 33 may automatically contract (snap back) and, in consequence, the inelastic region 61 in which substantially none of the first waist inner end elastic elements 33 is present may be formed. Similarly, the inelastic region 62 also may be formed.

In the inner end portion 36 of the front waist region 14, the first waist inner end elastic elements 33 intersect with the both side edge portions of the liquid-absorbent structure 11 so that the liquid-absorbent structure 11 may be kept in close contact with the wearer's body at a desired degree of fit to eliminate the likelihood that a gap causing leakage of the body exudates may be formed between the wearer's body and the liquid-absorbent structure 11 owing to the movement of the wearer's thighs. Meanwhile, the second waist inner end elastic elements 34 are not so arranged to intersect with the liquid-absorbent structure 11 and a contractile force thereof should not act upon the liquid-absorbent structure 11 and form gathers causing the leakage of body exudates.

\<Crotch Panel\>

The crotch panel 13 includes a base sheet 42 located in a central region in the transverse direction X and a pair of leg elasticized sheets 43 joined to the skin-facing surface of the base sheet 42 along both lateral portions thereof. The base sheet 42 includes a crotch interior layer 44 located on the side of the skin-facing surface and a crotch exterior layer 45 located on the side of the non-skin-facing surface. As material for these crotch interior and exterior layers 44, 45, various kinds of fibrous nonwoven fabrics or breathable plastic films both of well known art may be used. The crotch interior layer 44 is preferably formed of leakage-barrier plastic films considering that the crotch interior layer 44 is located to face the liquid-absorbent structure 11 and the crotch exterior layer 45 is preferably formed of fibrous nonwoven fabrics having a texture superior to that of plastic films considering that the crotch exterior layer 45 partially defines the exterior surface of the diaper 10.

The crotch panel 13 has front and rear end portions 46, 47 and an intermediate portion 48 extending between the front and rear end portions 46, 47. The front and rear end portions 46, 47 are fixed to the respective skin-facing surfaces of the front and rear elastic waist panels 18, 19 adjacent to the respective inner end edges 18a, 19a of the front and rear elastic waist panels 18, 19 via joining regions arranged on the non-skin-facing surfaces of the front and rear end portions 46, 47, respectively, and coated with, for example, hot melt adhesive.

\<Leg Elasticized Sheet\>

Each of the leg elasticized sheets 43 has a plurality of strand- or string-like leg elastic elements 50 and a leg sheet 51 to secure these leg elastic elements 50. The leg sheet 51 is formed of a single sheet of fibrous nonwoven fabrics or plastic sheet doubled up and fixed to the base sheet 42 in a joint region 41. The leg elastic elements 50 are interposed and contractibly secured under tension between the respective halves of the doubled-up leg sheet 51 with hot melt adhesive. The leg elastic elements 50 may be formed of string- or strand-like elastic materials having a fineness in a range of 310 to 620 dtex and a stretch ratio in a range of 2.0 to 3.0 times or of sheet-like elastic materials, for example, a sheet formed of urethane-based fiber having a given width and thickness. The leg elastic elements 50 include an inner side leg elastic element 50a arranged adjacent to the joint region 41 in which the leg elasticized sheet 43 is joined to the liquid-absorbent structure 11 and outer side leg elastic elements 50b arranged so as to be distanced outward in the transverse direction X from the inner side leg elastic element 50a.

Each of the leg elasticized sheets 43 has an elastic side flap 53 extending outward in the transverse direction X from a joint portion 49 in which the leg elasticized sheet 43 is joined to the liquid-absorbent structure 11. The elastic side flap 53 has front and rear portions (corresponding to the front and rear end portions 46, 47) fixed to the front and rear waist regions 14, 15 so as to extend outward in the transverse direction X from the joint region 41, an inelastic region 57A defined between the joint region and innermost one of the leg elastic elements 50a and an elastic region 57B (corresponding to the leg opening) in which the leg elastic elements 50 are arranged.

<Absorbent Structure>

The liquid-absorbent structure 11 has a longitudinally longer pad-like shape and includes front and rear end portions 54, 55, an intermediate portion 56, an absorbent core 58 extending in the longitudinal direction Y at least in the crotch region 16, a body side liner 59 located on the side of the skin-facing surface of the absorbent core 58 and an exterior cover 60 located on the side of the non-skin-facing surface of the absorbent core 58. The generally entire non-skin-facing surface of the liquid-absorbent structure 11 is distributed with hot melt adhesive in well known patterns. The front and rear end portions 54, 55 are respectively fixed to the skin-facing surfaces of the front and rear waist panels 18, 19 with the hot melt adhesive and the intermediate portion 56 also is fixed to the skin-facing surface of the crotch panel 13 with the hot melt adhesive.

Referring to FIG. 3, the front end portion 54 of the liquid-absorbent structure 11 is fixed to the skin-facing surface of the waist interior layer 24 of the elastic front waist panel 18 and the rear end portion 55 is interposed between the waist interior layer 25 and the waist exterior layer 27 of the elastic rear waist panel 19 and fixed to the skin-facing surface of the waist exterior layer 27. By fixing the front end portion 54 of the liquid-absorbent structure 11 to the skin-facing surface of the waist interior layer 25, it is ensured that the waist interior layer 24 which is elastically contractible and relatively flexible is put in direct contact with the wearer's skin and, in consequence, a texture is improved. Meanwhile, by fixing the rear end portion 55 between the waist interior layer 25 and the waist exterior layer 27, it is possible to prevent the body exudates from getting into direct touch with the wearer's skin even if the discharged body exudates diffuse from the crotch region 16 to the rear end portion 55 of the liquid-absorbent structure 11 located in the rear waist region 15. The front and rear end portions 54, 55 of the liquid-absorbent structure 11 are located outward of the front and rear end portions of the leg elasticized sheet 43 in the longitudinal direction Y, in other words, the dimension of the leg elasticized sheet 43 in the longitudinal direction Y is smaller than the dimension of the liquid-absorbent structure 11 in the longitudinal direction Y.

The absorbent core 58 has a mass per unit area in a range of about 400 to about 600 g/m2 and includes a core formed of wood fluff pulp, superabsorbent polymer particles (SAP) and optionally thermal fusion bonding staple fibers and liquid-permeable fibrous nonwoven fabrics covering the core. As material for the body side liner 59, various types of fibrous nonwoven fabrics of well known art such as liquid-permeable spunbonded nonwoven fabrics and SMS nonwoven fabrics each having a mass per unit area in a range of about 10 to about 30 g/m2 may be used. As material for the exterior cover 60, for example, liquid-impermeable spun-bonded nonwoven fabrics, SMS nonwoven fabrics, plastic sheets or laminate sheets of fibrous nonwoven fabrics and fibrous nonwoven fabrics each having a mass per unit area in a range of about 10 to about 30 g/m2 may be used.

Referring to FIGS. 1 through 4, the elastic regions 57B of the respective elastic side flaps 53 toward the wearer's body, while maintaining their outward extension in the transverse direction X. In the typical design such that a plurality of leg elastic elements are arranged side by side in the transverse direction X from the vicinity of the liquid-absorbent structure to the outermost peripheries of the respective leg openings, the elastic gathering action of the leg elastic elements arranged in the vicinity of the absorbent structure is inhibited under the influence of relatively high rigidity of the absorbent structure but the leg elastic elements arranged in the outer regions distanced outward from the absorbent structure exert a desired contractile force (elastic gathering action). Consequently, the dimension in the longitudinal direction of the outer regions correspondingly decreases and the respective leg-openings rise toward the wearer's body so as to form respective barrier-cuffs. According to the present embodiment, the respective elastic regions 57B in which the leg elastic elements 50 are arranged are distanced by a given dimension from the outer side edges of the liquid-absorbent structure 11 so that even the respective innermost leg elastic elements are not much affected by the relatively high rigidity of the liquid-absorbent structure 11 and the leg elastic elements 50 exert the elastic gathering action almost equally as a whole. Concerning the inelastic regions 57A, the dimension in the longitudinal direction Y of the regions in which the respective innermost leg elastic elements 50a are arranged becomes smaller than the dimension in the longitudinal direction Y of the joint regions 49 by the elastic gathering action of the respective innermost leg elastic elements 50a and, in consequence, the inelastic regions 57A stand up toward the wearer's body. Meanwhile, concerning the elastic regions 57B, the respective innermost elastic elements 50a are almost free from the influence of the relatively high rigidity of the liquid-absorbent structure 11 and contract almost equally to the remaining leg elastic elements. In this manner, in the diaper 10 put on the wearer's body, the respective elastic regions 57B maintain a planar state without standing up unlike the inelastic regions 57A and are put in contact with the wearer's body in the planar state.

To assure that, with the diaper 10 put on the wearer's body, the inelastic regions 57A of the respective elastic side flaps 53 stand up and the elastic regions 57B are kept in close contact with the wearer's body in the planar state at a degree of desired fit, a dimension W4 in the transverse direction X of the respective inelastic regions 57A is preferably in a range of about 10 to about 25 mm and a dimension W5 in the transverse direction X of the respective elastic regions 57B is preferably in a range of about 20 to about 35 mm. If the dimension W4 in the transverse direction X of the inelastic region 57A is about 10 mm or less, innermost leg elastic member 50a may be affected by relatively high rigidity of the absorbent structure and if the dimension W4 is about 25 mm or more, the inelastic region 57A expected to stand up may be rolled up or collapse. Meanwhile, if the dimension W5 in the transverse direction X of the elastic region 57B is about 20 mm or less, the elastic region 57B may not extend outward in the transverse direction X in the planar state but may rise together with the inelastic region 57A. In contrast, if the dimension W5 is about 35 mm or more, the dimension W4 of the inelastic region 57A will become relatively reduced in its size and the innermost leg elastic member 50a may be affected by the relatively high rigidity of the liquid-absorbent structure 11 and it might become impossible for the elastic region 57B to maintain the planar state. A ratio of the dimension W4 in the transverse direction X of the inelastic region 57A versus the dimension W3 in the transverse direction X of the elastic side flap 53 (i.e., W3/W4) is preferably in a range of about 22 to about 56%. As has previously been described, it is required that the respective innermost leg elastic elements 50a are distanced from the associated joint regions 49 by a given dimension to ensure the advantageous effects of the present invention. However, this requirement is further specified as described below. If the ratio of the dimension W4 in the transverse direction of the inelastic region 57A versus the dimension W3 in the transverse direction of the elastic side flap 53 is about 22% or less, the contraction of the innermost elastic member 50a might be affected by the high stiffness of the liquid-absorbent structure 11. Meanwhile, if this dimensional ratio is 56% or more, the inelastic regions 57A adapted to rise may become relatively large, restricting the leg-openings 23 in size and, in addition, the absorbent structure may be spaced downward from the wearer's body, making a smooth movement of the wearer's thighs difficult. The various dimensions L1, L2, W1, W2 and W3 as have been described above or as will be described later are values measured on the diaper 10 having been stretched in the longitudinal direction Y and the transverse direction X until none of gathers formed by the elastic gathering action (elastic contraction) of the elastic elements is observed.

It is possible to set an elastic gathering action of the outer side leg elastic elements 50b to be lower than that of the innermost leg elastic member 50a or to set the elastic gathering action of the leg elastic elements to become gradually lower from the innermost side to the outermost is in a range of about 300 to about 425 mm, a dimension L2 in the longitudinal direction Y of the crotch region 16 is in a range of about 205 to about 270 mm, a dimension L3 in the longitudinal direction Y of the side edges 18d of the front waist region 14 (corresponding to a dimension in the transverse direction X of the side edges 19d of the rear waist region 15) is in a range of about 95 to about 145 mm, and a dimension W2 in the transverse direction X of the crotch panel 13 is in a range of about 185 to about 240 mm. While the ratio of the dimension in the transverse direction of the crotch region versus the dimension in the transverse direction of the diaper is about 50% or less in the conventional pull-on disposable diapers, this dimensional ratio, i.e., the ratio of the dimension W2 versus the dimension W1 (W1/W2) is in a range of about 55 to about 70%.

Usually for the pull-on disposable diaper, especially for diapers of three connecting piece structure, if the dimensional ratio (W1/W2) is about 55% or more, the leg-openings will become relatively narrow, making it difficult to pass the legs through the leg-openings in the course of putting the diaper on the wearer's body, and the leg-openings may be partially broken if it is forcibly tried to pass the legs through the leg-openings. According to the present embodiment, in contrast, it is not the elastic side flap 53 as a whole which rises toward the wearer's body but only the respective elastic regions 57B in the respective side flaps 53 are put in close contact with the wearer's body in the planar state. In this manner, leakage of the body exudates is reliably prevented such that the wearer's thighs are not excessively tightened up.

TABLE 1

| | Width dimension W2 (mm) of crotch panel | Width dimension W1 (mm) of elastic waist panel | Dimensional ratio (W2/W1) | Buttocks-covering effect immediately after diaper has been put on | Buttocks-covering effect 30 min. after diaper was put on | Convenience for putting diaper on wearer's body |
|---|---|---|---|---|---|---|
| Embodiment 1 | 210 | 370 | 57% | A | A | A |
| Embodiment 2 | 210 | 345 | 61% | A | A | A |
| Embodiment 3 | 210 | 320 | 66% | A | A | A |
| Embodiment 4 | 220 | 370 | 59% | A | A | A |
| Embodiment 5 | 195 | 345 | 57% | A | A | A |
| Embodiment 6 | 195 | 320 | 61% | A | A | A |
| Embodiment 7 | 190 | 345 | 55% | A | A | A |
| Embodiment 8 | 230 | 345 | 67% | A | A | B |
| Comparative example 1 | 160 | 370 | 43% | C | C | A |
| Comparative example 2 | 160 | 345 | 46% | C | C | A |
| Comparative example 3 | 170 | 320 | 53% | A | C | A |
| Comparative example 4 | 180 | 370 | 49% | C | C | A |
| Comparative example 5 | 180 | 345 | 52% | C | C | A |
| Comparative example 6 | 180 | 340 | 53% | C | C | A |
| Comparative example 7 | 250 | 345 | 72% | A | A | C | side so that the elastic region 57B may more reliably extend in the transverse direction X and may be more reliably kept in close contact in a planar state with the wearer's body at a desired degree of fit. In a consequence of such manner of setting, a dimension of the region in which the outer side leg elastic elements have contracted becomes larger than a dimension of the region in which the innermost leg elastic element has contracted, causing the leg elasticized sheet 43 to sag in the vicinity of the outer side edge thereof, thereby making it possible for the elastic region 57B to maintain the planar state further stably.

Referring to FIG. 2, a dimension L1 in the longitudinal direction Y of the diaper 10 is in a range of about 420 to about 540 mm, a dimension W1 in the transverse direction X of the diaper 10 (corresponding to a distance dimension in the transverse direction X between both rows of the seams)

<Evaluating Method Relating to Dimensional Ratio (W2/W1)>

Table 1 lists dimensional ratio between the width dimension W2 of the crotch panel 13 versus the width dimension W1 of the elastic waist panel 12 measured on the embodiments 1 through 8 and the comparative examples 1 through 7 of the diaper of three connecting piece structure similar to the present embodiments but having different sizes and the evaluation result relating to the dimensional ratio W2/W1. In this regard, the measurement was conducted on the diaper 10 stretched in the longitudinal direction Y and in the transverse direction X until the wrinkles by the elastic gathering action of the elastic elements disappear. As an evaluating method relating to dimensional ratio (W2/W1), the inventors requested mothers to put the diapers according to the respective embodiments and the respective comparative examples on their babies (a total of 20 babies) and to evaluate in three steps, i.e., "good", "no opinion" and "not very good" concerning three items as follow: "the state in which the wearer's buttocks are covered with the diaper immediately after the diaper has been put on the wearer's body", "the state in which the wearer's buttocks are covered with the diaper 30 minutes after the diaper has been put on the wearer's body" and "convenience of putting the diaper on the wearer's body". The case in which 70% or more of the mothers answered "good" for the respective items was scored as "A", the case in which 50% or more of the mothers answered "good" was scored as "B" and the case in which 50% or less (10 or less) of the mothers answered "good" was scored as "C". In this regard, the term "convenience of putting the diaper on the wearer's body" used herein is based on whether the diaper was smoothly handled without a trouble such that the wearer's toes may be caught by the leg-openings when the wearer's legs were guided to pass through the leg-openings.

As indicated in Table 1, the diapers according to the embodiments 1 through 8 in which the dimensional ratio (W2/W1) is in a range of about 55 to about 70% irrespective of the diaper sizes were evaluated as "A" or "B" with respect to the three items as have been defined above. Meanwhile, the diapers according to the comparative examples 1 through 7 in which the dimensional ratio (W2/W1) is in a range of about 43 to about 53% and of 72% irrespective of the diaper sizes were evaluated as "C" with respect to at least one of the three items. Specifically, the comparative example 3 in which the dimensional ratio was 53% was scored as "C" with respect to the item "the state in which the wearer's buttocks are covered with the diaper 30 minutes after the diaper has been put on the wearer's body". In contrast, the comparative example 7 in which the dimensional ratio was 72% was scored as "C" with respect to the item "convenience of putting the diaper on the wearer's body". More specifically, if the dimensional ratio is about 55% or less, the wearer's buttocks will be certainly covered with the diaper immediately after the diaper has been put on the wearer's body but the buttocks may be exposed after a few minutes due to, for example, the movement of lower part of the wearer's body. If the dimensional ratio is about 70% or more, the crotch region covers the buttocks over a relatively wide range and the buttocks should not exposed in the course of putting the diaper on the wearer's body as well as after the diaper has been put on the wearer's body. However, the leg-openings will be correspondingly narrowed, making it difficult to pass the wearer's legs through the leg-openings when it is tried to put the diaper on the wearer's body.

Figure 5:
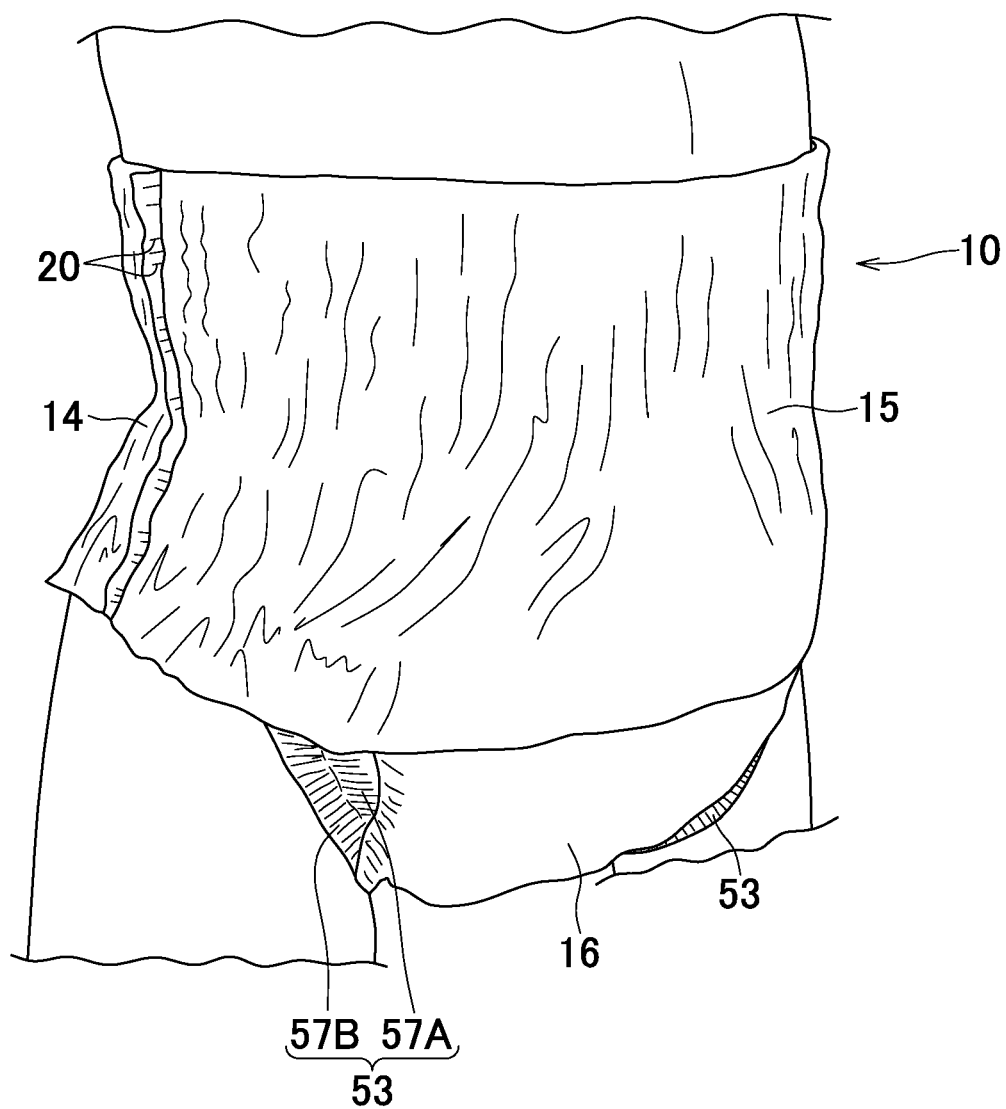
FIG. 5 is a perspective back view of the diaper put on the wearer's body.

Referring to FIG. 5, the crotch region 16 has a sufficient width dimension to cover the wearer's buttocks completely on the side of the rear waist region 15. The elastic regions 57B of the respective elastic side flaps 53 are kept in close contact with the wearer's thighs in a planar state without rising toward the crotch region of the wearer and, in consequence, the elastic regions (corresponding to the leg-openings) should not be tucked in the buttock-cleavage and exposed to the outside. Also on the side of the crotch region 16 adjacent to the front waist region 14, the elastic regions 57B are kept in close contact with the wearer's thighs in a planar state and, in consequence, the leg-openings should not be rolled-up owing to movements of thighs.

The regions of the elastic waist panel 12 of the diaper 10 put on the wearer's body, in which the front and rear end portions 54, 55 of the liquid-absorbent structure 11 are present, include the intermediate portions 37, 40 in which none of first and second waist elastic elements 31, 32 and first and second waist inner end elastic elements 33, 34 is arranged and the inelastic regions 61, 62 in which none of the first and second waist inner end elastic elements 33, 34 is not arranged. Consequently, there is no possibility that the contractile force of the respective elastic elements 31, 32, and first and second waist inner end elastic elements 33, 34 may act on the semi-rigid absorbent core 58 having a flexural rigidity (bending stiffness) higher than that of the sheet members so as to reduce the width dimension of the absorbent core 58. In other words, it is possible to put the absorbent structure in close contact with the wearer's body in a state sufficiently extending also in the transverse direction.

As will be apparent from the related Figures, the inner end edges of the front and rear waist panels 18, 19 are preferably coincident with the inner end edges of the front and rear waist regions 14, 15 and the inner end portions of the front and rear waist panels 18, 19 preferably extend not into the crotch region 16 and, even if extend into the crotch region 16, a dimension in the longitudinal direction Y of these end portions extending into the crotch region 16 is preferably 10 mm or less. According to the present embodiment, a large proportion of the leg-openings is formed of the leg elasticized sheet 43 so as to be stably kept in close contact with the wearer's body at a desired degree of fit. In consequence, even when the diaper has the three piece structure, the leg openings should not be tucked in the cleavage of the buttocks, and the buttocks should not be exposed. For this reason, it is not required for the front and rear waist panels 18, 19 to extend partially into the crotch region 16. The inner end portions of the front and rear waist panels 18, 19 extend not into the crotch region 16 (if extend thereinto, only by 10 mm or less) and whereby movements of the thighs should not be inhibited than when the inner end portions significantly extend into the crotch region 16.

Second Embodiment

The diaper 10 according to this embodiment is similar to the first embodiment as far as the basic arrangement is concerned but distinguished from the first embodiment in aspects described below.

Figure 6:
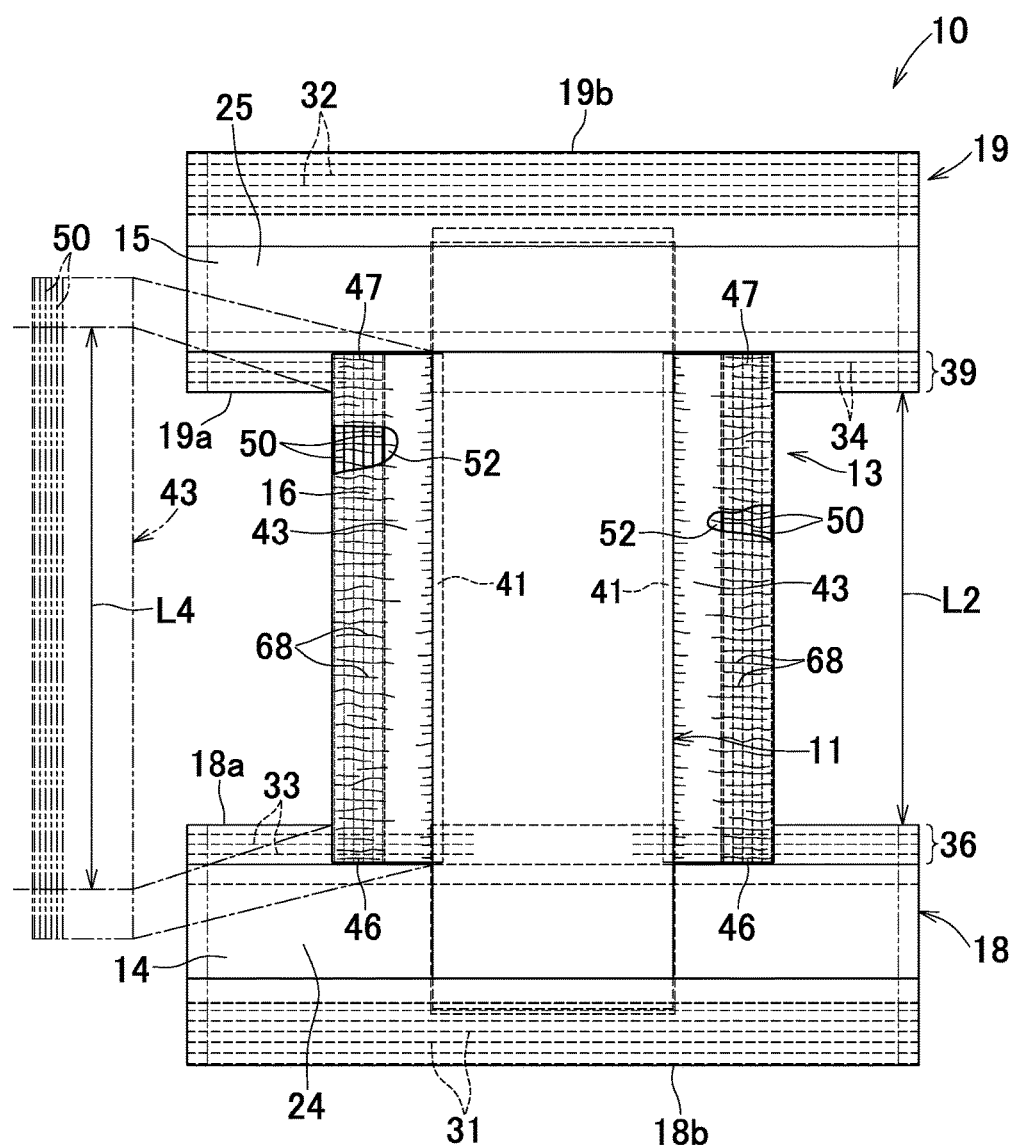
FIG. 6 is a partially cutaway developed plan view of the diaper according to a second embodiment.

According to this embodiment, as illustrated in FIG. 6, the respective elasticized sheets 43 are fixed as in a contractile state to the respective skin-facing surfaces of the base sheet 42 and the inner end portions 36, 39 of the front and rear waist regions 14, 15, and consequently the leg elasticized sheets 43 are formed with a number of gathers 68. The gathers 68 are arranged in rows in the longitudinal direction so as to extend in the transverse direction not only in the regions in which the leg elastic elements 50 are arranged but also in the joint regions 41 in which the leg elasticized sheets 43 are fixed to the base layer 42. The leg elastic elements 50 is secured to the leg sheets 51 with hot melt adhesive circumferentially distributed to the leg elastic elements 50 continuously or continually in the longitudinal direction Y. In the inelastic regions 57A of the respective leg elasticized sheets 43, elongate reinforcing sheets 52 are interposed between the respective doubled up leg sheets 51 and fixed therebetween with hot melt adhesive to prevent the leg elasticized sheets 43 may be broken in the vicinity of the joint regions 49.

The dimension in the longitudinal direction Y of the crotch region 16, i.e., the distance dimension L2 in the longitudinal direction Y between the inner end edge 18a of the front waist region 14 and the inner end edge 19a of the rear waist region 15 is in a range of 205 to 270 mm and a usable elongated dimension L4 of leg elasticized sheets 43 at maximum elongation is in a range of about 225 to about 380 mm. The term "usable elongated dimension L4" used herein means the longitudinal dimension of the respective extensible/contractible portions of the leg elasticized sheets 43 defined between the inner end edge 18a of the front waist region 14 and the inner end edge 19a of the rear waist region 15 except the front and rear end portions 46, 47 fixed to the front and rear waist regions 14, 15, respectively, and being substantially inextensible. The leg elasticized sheets 43 are elastically extensible to the dimension at least 1.05 times or more, preferably 1.05 to 1.5 times, further preferably 1.1 to 1.4 times of the dimension L2 in the longitudinal direction Y of the crotch region. The leg elasticized sheets 43 may be attached in the contractile state (in overfeeding fashion) and length dimension of the respective leg-openings may be optionally set by controlling a degree of overfeeding to enlarge a range of the proper size for the wearer's body size.

The dimensional ratio of the leg elasticized sheets 43 included in the diaper 10 in the form of a product before and after contraction may be measured using test pieces prepared by cutting out, together with the base sheet 42, the leg elasticized sheet 43 joined to the side edge of the base sheet 42 in the crotch region 16. Specifically, the base sheet 42 and the leg elasticized sheet 43 adjacent to the joint region 41 in the crotch region 16 of the diaper 10 may be cut out along the longitudinal direction Y with the inclusion of the joint region 41 to prepare a test piece having an optional length (e.g., 100 mm). The test piece is prepared so as to have a rectangular shape. Then, the sheet member forming the base sheet 42 and the leg elasticized sheet 43 are cut out along a given width (e.g., 50 mm) from the region adjacent to the joint region 41 to prepare the other test piece and dimensions in the longitudinal direction Y of the respective test pieces are measured. The leg elasticized sheet 43 is joined in the contractile state to the side edge of the base sheet 42 and consequentially the dimension of the sheet member (i.e., the leg sheet 51) is larger than the dimension of the sheet member forming the base sheet 42. In view of this, the dimensional ratio before and after contraction of the leg elasticized sheet 43 may be calculated from the dimensional ratio between the sheet element forming the leg elasticized sheet 43 and the sheet element forming the base sheet 42.

Figure 7:
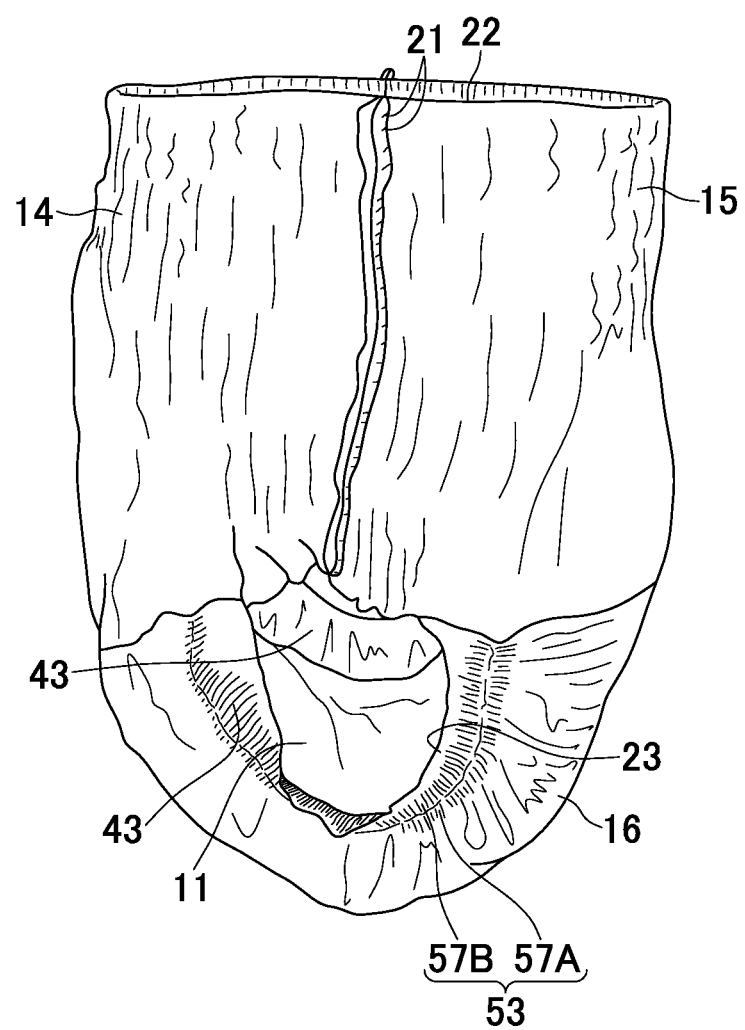
FIG. 7 is a side perspective view of the diaper according to the second embodiment put on the wearer's body.

Referring to FIG. 7, when the waist-opening is broadened to guide the wearer's legs through the leg-openings in the course of putting the diaper 10 on the wearer's body, the joint regions 57B of the respective side flaps 53 are not stretched but project outward in the transverse direction X and sag at the lower ends of the leg-openings 23. For this reason, even if the ratio of the dimension W2 in the transverse direction X of the crotch region 16 versus the dimension W1 in the transverse direction X of the diaper 10 is about 55% or more, the joint regions 57B never stand up toward the wearer's body but project outward in the transverse direction X in the course of putting the diaper 10 on the wearer's body. In this manner, the leg-opening should not be narrowed and the wearer's toes should not be caught by the leg-openings.

To attach the leg elasticized sheet 43 in a contractile state, i.e., in the state entirely formed with a number of gathers 68, to the leg sheet 51, the leg elasticized sheet 43 may be attached, in a contractile state, to the leg sheet 51 or the leg elasticized sheet 43 may be subjected to a gear-orientation treatment to form the leg elasticized sheet 43 with a number of gathers 68 before the leg elasticized sheet 43 is attached to the leg sheet 51.

Third Embodiment

The diaper 10 according to this embodiment is similar to the first embodiment as far as the basic arrangement is concerned but distinguished from the first embodiment in aspects described below.

Figure 8:
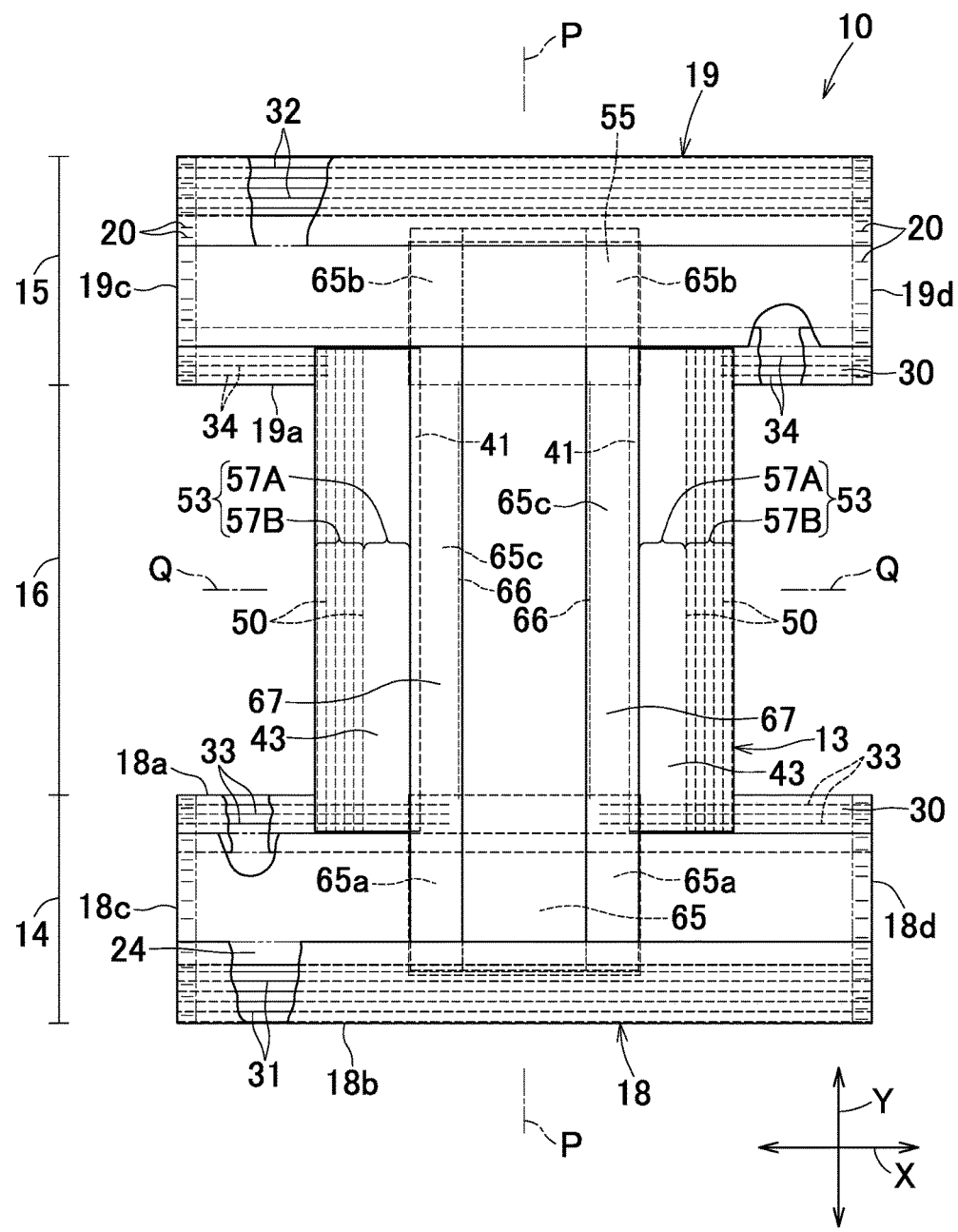
FIG. 8 is a developed plan view of the diaper according to a third embodiment.
Figure 9:
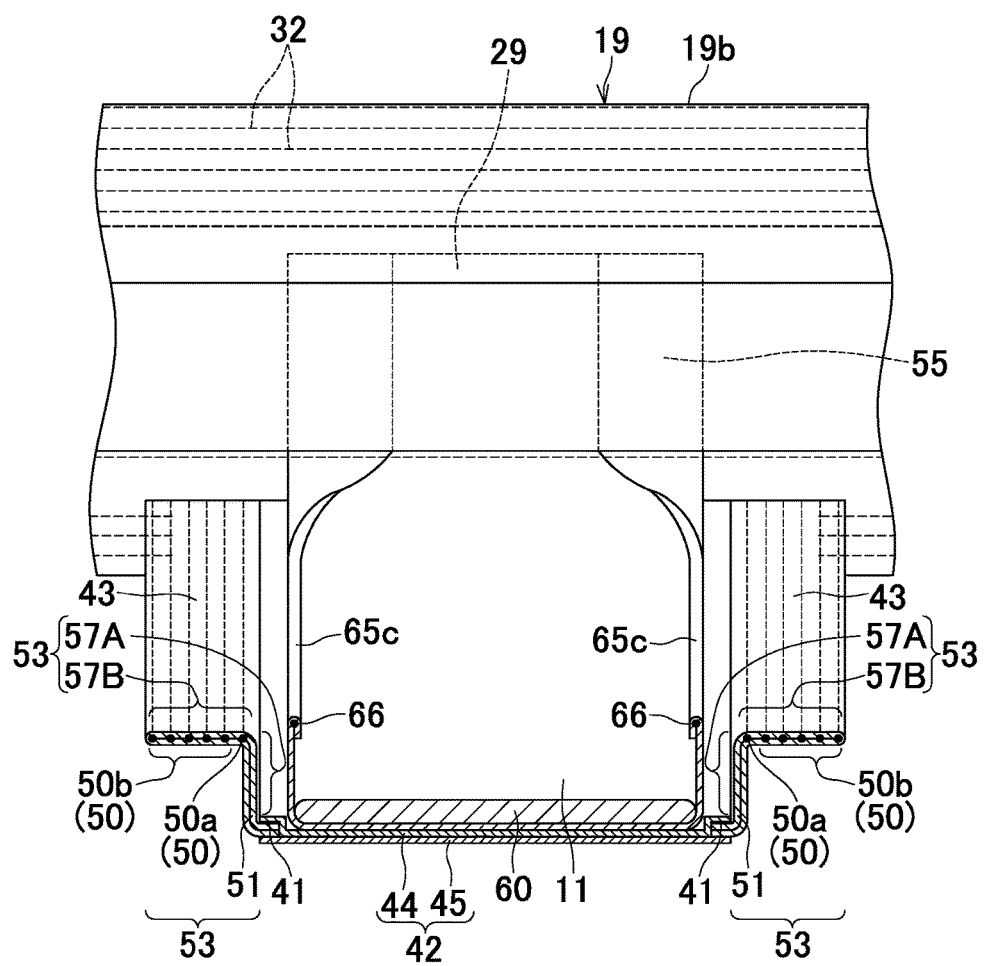
FIG. 9 is a partial sectional view similar to FIG. 4, illustrating the third embodiment.
Figure 10:
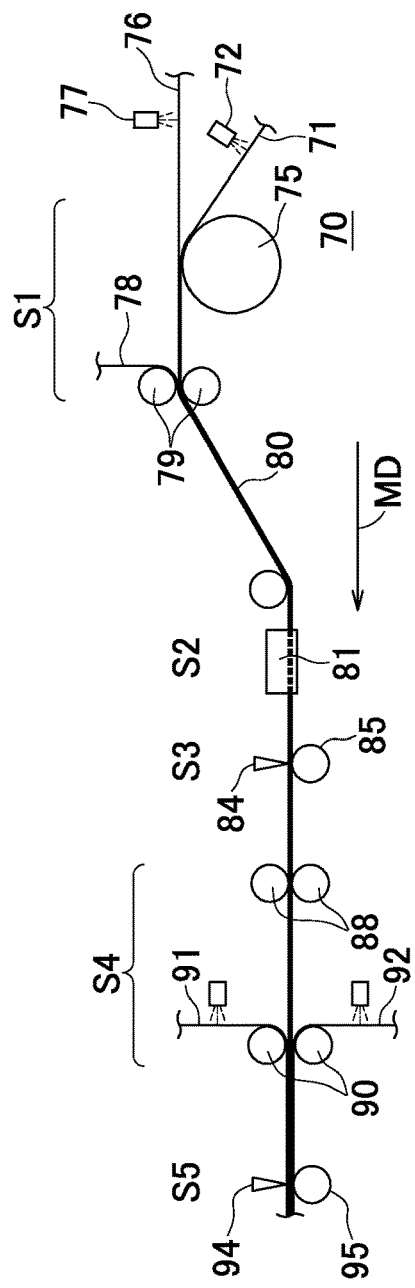
FIG. 10 (a) is a schematic diagram of a manufacturing apparatus for a crotch panel according to the second embodiment and FIG. 10 (b) illustrates a composite web in a step of manufacturing the crotch panel according to the second embodiment.
Figure 10:
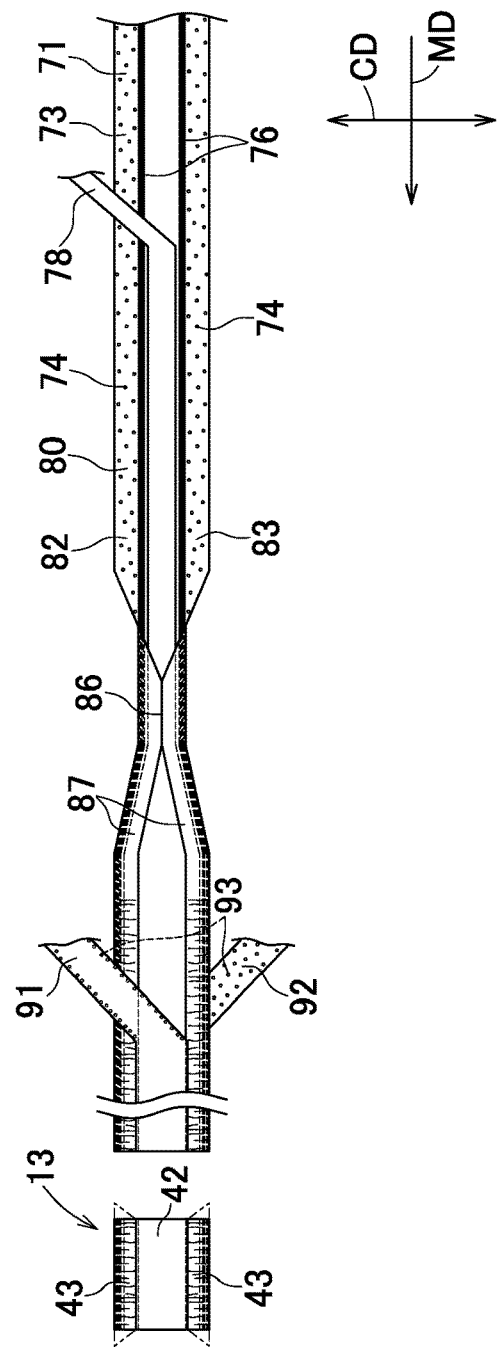

Referring to FIG. 8, according to this embodiment, a barrier sheet 65 formed of liquid-impermeable fibrous nonwoven fabrics, plastic films or laminates thereof is located on the surface of the liquid-absorbent structure 11 facing the base sheet 42. Both side edge portions of the barrier sheet 65 are folded toward the skin-facing surface of the liquid-absorbent structure 11 and each of the side edge portions has a proximal edge portion, front and rear fixed end portions 65a, 65b fixed to the sin-facing surface of the liquid-absorbent structure 11 in the front and rear waist regions 14, 15 and a distal edge portion 65c formed by further folding the inner side edge portion of the barrier sheet 65 inward and extending in the direction of the longitudinal axis P. A string- or strand-like cuff elastic element 66 extending in the longitudinal direction Y is contractibly arranged under tension within the distal edge portion 65c. In the diaper 10 put on the wearer's body, the distal edge portions 65c are distanced from the skin-facing surface of the liquid-absorbent structure 11 under the contraction of the cuffs elastic elements 66 to forma pair of the barrier cuffs.

According to the present invention, as described above, the respective elastic regions 57B of the elastic side flaps 53 extend outward in the transverse direction X in a planar state and, for this reason, the size of the leg-openings should not be restricted even if the dimension W2 in the transverse direction X of the crotch region 16 is relatively large. However, a gap may be left between the thighs and the leg-openings depending on the size of the wearer's thighs. The crotch region 16 is provided with the barrier-cuffs 67 so that double barriers may be defined by the liquid-impermeable barrier cuffs and the respective inelastic regions 57A of the elastic side flaps 53, and whereby leakage of body exudates may be effectively prevented.

<Crotch Panel Manufacturing Step>

FIG. 10(a) is a schematic diagram illustrating a manufacturing apparatus for the crotch panel according to the second embodiment and FIG. 10(b) is a schematic diagram illustrating a continuous composite web in the manufacturing process for the crotch panel. Referring to FIG. 10(a), a manufacturing apparatus 70 for the crotch panel 13 exemplarily illustrated therein includes an attachment step S1, a folding step S2, a first cutting step S3, a contraction/assembling step S4 and a second cutting step S5 in this order in a machine direction MD.

<Continuous Elastic Element Attachment Step S1>

A first web 71 as base material of the leg sheet 51 is fed from a feed roller and, at a coater station 72, side edge portions of a first surface 73 of the web 71 opposed to each other in a cross direction CD is coated with hot melt adhesive 74. The first web 71 is fed to a rotary drum 75 and simultaneously a pair of continuous elastic elements 76 as base material of the leg elastic elements 50 are fed onto the first surface 73 of the first web 71. At another coater station 77, the continuous elastic elements 76 have previously been coated around entire circumference thereof with hot melt adhesive continuously in the machine direction MD and fixed to the first surface 73 of the first web 71 with this hot melt adhesive. Then the first web 71 and second web 78 as base material for the reinforcing sheet 52 are fed between a pair of press rollers 79 are pressed together so that the second web 78 may be located on the first surface 73 of the first web 71 between the pair of continuous elastic elements 76. The surface of the second web 78 facing the first surface 73 of the first web 71 has been coated with hot melt adhesive and, with this hot melt adhesive, the second web 78 is fixed to the first web 71 to form a composite web 80.

<Folding Step S2>

Both side edge portion 82, 83 of the composite web 80 opposed to each other in the cross direction CD are folded inward with use of folding guide plates 81 and the respective halves of each side edge portions folded inward in this manner are fixed to each other with hot melt adhesive 74 together with the continuous elastic elements 76 interposed therebetween.

<First Cutting Step S3>

The composite web 80 is fed to pass between a cutter 84 and an anvil roller 85 opposed to each other and to be cut a central region 86 as viewed in the cross direction CD so that a separation line 87 may be defined and the composite web 80 may be split up in two along the separation line 87.

<Contracting/Assembling Step S4>

The composite web 80 is fed to pass through a pair of circumferential velocity regulating rollers 88 opposed to each other. Then, a third webs 91, 92 as base material for the crotch interior layer 44 and the crotch exterior layer 45 are fed via a pair of feed rollers 90 to the first surface 73 and the surface opposite thereto of the composite web 80. The both side edge portions of the third webs 91, 92 have previously been coated with hot melt adhesive 93 and, with this hot melt adhesive 93, the split region is fixed. A circumferential velocity V1 of the circumferential velocity regulating rollers 88 is higher than a circumferential velocity V2 of the feed rollers 90 and a ratio of the circumferential velocity V1 versus the circumferential velocity V2 (V1/V2'100) is in a range of about 105 to about 150%, preferably in a range of about 110 to about 140%. In other words, the circumferential velocity regulating rollers 88 rotate at a circumferential velocity at 1.05 to 1.5 times, preferably 1.1 to 1.4 times of the circumferential velocity V2 of the feed rollers 90. Consequently, the split region 87 contracts in the course between the circumferential velocity rollers 88 and the feed rollers 90 and a larger quantity of the composite web 80 per unit time (sec) to the feed rollers 90 compared to the other steps S1 to S3. In this way, the split region 87 are attached in a contracted state to the third webs 91, 92.

<Second Cutting Step S5>

The composite web 80 is fed to pass between a cutter 94 and an anvil roller 95 opposed to each other and cut along a cut line extending in the cross direction CD to form a plurality of the crotch panels 13. While each of the respective crotch panels 13 is extensible in the region in which the leg elastic elements 50 for the leg elasticized sheet 43 are arranged, the crotch panel 13 may be attached to the elastic waist panel 12 after the crotch panel 13 have been caused to contract to the length dimension L2 in the longitudinal direction Y of the crotch region 13.

Method to attach the leg elasticized sheet 43 in a contracted state to the base sheet 42 is not limited to the method as has been described above but it is possible, for example, to use a pair of gear rollers as the circumferential velocity regulating rollers so that the leg elasticized sheet 43 may be mechanically shaped to become wavy and attached in such state to the base sheet 42.

The constituent elements of the disposable diaper 10 are not limited to those described in the specification but the other various types of material widely used in the relevant technical field may be used without limitation unless otherwise stated. The terms "first" and "second" used in the specification and claims of the present invention are not ordinal numbers but used merely to distinguish the similar elements, similar positions or the other similar items.

The disclosure relating to the wearing article according to the present invention described hereinabove may be arranged at least as follows:

A pull-on disposable wearing article having a longitudinal direction and a transverse direction and including skin-facing surface/non-skin-facing surfaces, a front waist region, a rear waist region, a crotch region extending between the front and rear waist regions, a front waist panel defining the front waist region, a rear waist panel defining the rear waist region, a crotch panel defining the crotch region and an absorbent structure attached to the skin-facing surface of the crotch panel and extending across the crotch region into the front and rear waist regions.

The wearing article further includes the following features: the elastic front and rear waist panels respectively have elastic regions defined on the outer side in the transverse direction of front and rear end portions of the absorbent structure and inelastic regions defined in a region in which the absorbent structure is present; the crotch panel has a pair of elastic side flaps located outside both side edges of the absorbent structure as viewed in the transverse direction and extending in the longitudinal direction; each of the elastic side flaps has front and rear end portions fixed to the front and rear waist regions so as to extend outward in the transverse direction, inelastic regions defined outside each of both side edges of the absorbent structure as viewed in the transverse direction and an elastic region defined outward of the inelastic region as viewed in the transverse direction; and a dimensional ratio in the transverse direction of the crotch panel versus a dimension in the transverse direction of the front and rear waist regions is in a range of about 55 to about 70%.

The pull-on disposable diaper according to the present invention disclosed in the above paragraph may include embodiments at least as described below:

(1) The front and rear waist panels respectively extend from the interior end edges of the front and rear waist regions into the crotch region by a dimension in a range of about 0 to about 10 mm.

(2) A dimensional ratio of a dimension in the transverse direction of the inelastic region versus a dimension in the transverse direction of the respective elastic side flaps is in a range of about 22 to about 56%.

(3) A dimension in the transverse direction of the inelastic region is in a range of about 10 to about 25 mm and a dimension in the transverse direction of the elastic region is in a range of about 25 to about 35 mm.

(4) The crotch panel includes a base sheet and a pair of leg elasticized sheets having elastically contractible leg elastic elements; respective portions of the leg elasticized sheets extending from joint regions in which the leg elasticized sheets are joined to the crotch panel to respective outer side edges define the respective elastic side flaps; the inelastic regions are defined by regions extending from the joint region to the respective innermost leg elastic elements; the elastic regions are defined by regions in which leg elastic elements are arranged; and the joint regions are joined, in a state formed with a number of gathers extending in parallel one with another in the transverse direction, to the crotch panel.

(5) The crotch region is provided with a barrier sheet and both lateral portions of the barrier sheet extending outward in the transverse direction from the both side edges of the absorbent structure define barrier-cuffs including front and rear fixed portions fixed to the skin-facing surface of the absorbent structure, distal edge portions extending in the longitudinal direction between the front and rear fixed end portions and cuffs elastic elements attached to the distal edge portions so that the barrier-cuffs rise under the contraction of the cuffs elastic elements.

The invention claimed is:

1. A pull-on disposable wearing article, comprising:
a longitudinal direction and a transverse direction,
a skin-facing surface and a non-skin-facing surface,
a front waist region,
a rear waist region,
a crotch region extending between the front and rear waist regions,
a front waist panel defining the front waist region,
a rear waist panel defining the rear waist region,
a crotch panel defining the crotch region, and
an absorbent structure attached to the skin-facing surface at the crotch panel and extending across the crotch region into the front and rear waist regions,
wherein
the front waist panel has a front elastic region and a front inelastic region, the front elastic region and the front inelastic region overlapping the absorbent structure,
the rear waist panel has a rear elastic region not overlapping the absorbent structure, and a rear inelastic region overlapping the absorbent structure,
the crotch panel has a pair of elastic side flaps located outside both side edges of the absorbent structure in the transverse direction and extending in the longitudinal direction,
each of the elastic side flaps has
front and rear end portions fixed to the front and rear waist regions, respectively, so as to extend outward in the transverse direction,
an inelastic region extending in the longitudinal direction and located outside the both side edges of the absorbent structure in the transverse direction, and
an elastic region extending in the longitudinal direction in parallel with the inelastic region and located outside the inelastic region in the transverse direction, wherein a plurality of leg elastic elements extending in the longitudinal direction are extensible and contractibly arranged in the elastic region,
a ratio of a dimension of the crotch panel in the transverse direction versus a dimension of one of the front and rear waist regions in the transverse direction is in a range of about 55 to about 70%,
the front waist region has an inner end portion extending in the transverse direction along an inner end edge of the front waist region, and a plurality of first waist inner end elastic elements extending in the transverse direction are arranged in the front elastic region at the inner end portion of the front waist region,
the rear waist region has an inner end portion extending in the transverse direction along an inner end edge of the rear waist region, and a plurality of second waist inner end elastic elements extending in the transverse direction are arranged in the rear elastic region at the inner end portion of the rear waist region,
the first and second waist inner end elastic elements are arranged so as to be distanced from each other in the transverse direction, respectively,
the first waist inner end elastic elements intersect with the both side edges of the absorbent structure, and the second waist inner end elastic elements are free from intersecting with the both side edges of the absorbent structure, and
each of the elastic side flaps has an inner end directly joined to the crotch panel at a joint region outside the absorbent structure in the transverse direction.

2. The wearing article according to claim 1, wherein the front and rear waist panels respectively extend from the inner end edges of the front and rear waist regions into the crotch region by a dimension in a range of about 0 to about 10 mm.

3. The wearing article according to claim 1, wherein a ratio of a dimension of the inelastic region in the transverse direction versus a dimension of the respective elastic side flap in the transverse direction is in a range of 22 to 56%.

4. The wearing article according to claim 1, wherein a dimension of the inelastic region in the transverse direction is in a range of 10 to 25 mm, and a dimension of the elastic region in the transverse direction is in a range of 25 to 35 mm.

5. The wearing article according to claim 1, wherein the crotch panel includes:
a base sheet, and
a pair of leg elasticized sheets having the elastically extensible/contractible leg elastic elements;
respective portions of the leg elasticized sheets extending from joint regions in which the leg elasticized sheets are joined to the crotch panel to respective outer side edges define the respective elastic side flaps;
the inelastic regions are defined by regions extending from the joint regions to the respective innermost leg elastic elements;
the elastic regions are defined by regions in which the leg elastic elements are arranged; and
the joint regions are joined, in a state formed with a number of gathers parallel one with another in the transverse direction, to the crotch panel.

6. The wearing article according to claim 1, wherein the crotch region is provided with a barrier sheet,
both lateral portions of the barrier sheet extending outward in the transverse direction from the both side edges of the absorbent structure define barrier-cuffs, and
the barrier-cuffs include
front and rear fixed portions fixed to the skin-facing surface of the absorbent structure,
distal edge portions extending in the longitudinal direction between the front and rear fixed end portions, and
cuffs elastic elements attached to the distal edge portions to cause the barrier-cuffs to rise under contraction of the cuffs elastic elements.

* * * * *